United States Patent
Alaodat

(10) Patent No.: US 12,419,928 B1
(45) Date of Patent: Sep. 23, 2025

(54) COMPOSITION AND METHOD FOR INDUCING NATURAL CONCEPTION

(71) Applicant: Ahmad Alaodat, Ar'ara BaNegev (IL)

(72) Inventor: Ahmad Alaodat, Ar'ara BaNegev (IL)

( * ) Notice: Subject to any disclaimer, the term of this patent is extended or adjusted under 35 U.S.C. 154(b) by 0 days.

(21) Appl. No.: 19/064,774

(22) Filed: Feb. 27, 2025

(51) Int. Cl.
| | |
|---|---|
| *A61K 36/736* | (2006.01) |
| *A61K 9/00* | (2006.01) |
| *A61K 9/06* | (2006.01) |
| *A61K 36/54* | (2006.01) |
| *A61K 36/9066* | (2006.01) |
| *A61P 15/08* | (2006.01) |

(52) U.S. Cl.
CPC .......... *A61K 36/736* (2013.01); *A61K 9/0036* (2013.01); *A61K 9/06* (2013.01); *A61K 36/54* (2013.01); *A61K 36/9066* (2013.01); *A61P 15/08* (2018.01)

(58) Field of Classification Search
CPC ...... A61K 36/736; A61K 9/0036; A61K 9/06; A61K 36/54; A61K 36/9066; A61P 15/08
See application file for complete search history.

(56) References Cited

FOREIGN PATENT DOCUMENTS

CN          112843182 A  *  5/2021  ........... A61K 31/045

OTHER PUBLICATIONS

Alwosta, "Kilwa—Wild Tibet Fruit (Sin Al Qamar, Qors Al Qamar, Yin YangZi)", <URL:www.alwosta.tn/en/herbs-and-seeds/727-kilwa-wild-tibet-fruit-sin-al-qamar-qors-al-qamar-yin-yangzi.html>, 2017 (archived online Apr. 24, 2022), 2 pages. (Year: 2017).*
Mao S, CN 112843182 A, Machine translation (Year: 2021).*
Wilson DR, "Natural Treatments for Blocked Fallopian Tubes" HealthlineMedia <URL:www.healthline.com/health/pregnancy/tubal-ligation-reversal#alternatives>, 2025, 14 pages (Year: 2025).*

* cited by examiner

*Primary Examiner* — Aaron J Kosar
(74) *Attorney, Agent, or Firm* — Shlomo Horowitz; Shlomo Horowitz Patents and Intellectual Property Ltd.

(57) ABSTRACT

A composition includes a mixture of a first powder taken from inside a hard, chocolate-brown-colored wild Tibet fruit of a tree, cinnamon powder and turmeric powder. The combination of the cinnamon powder and the turmeric powder may constitute from 10% to 25% of the composition and wherein the first powder constitutes from 75% to 90% of the composition, in some versions. A paste may be made by adding water to the powder mixture. A method of overcoming blocked fallopian tube(s) may include administering the paste vaginally in a porous holder for example for several consecutive nights commencing after the woman's period and then abstaining from relations for a defined period of time. A method of preparing a device for use vaginally may include preparing the powder mixture, preparing the paste and placing the paste in a porous holder.

20 Claims, 2 Drawing Sheets

COMPOSITION AND METHOD FOR INDUCING NATURAL CONCEPTION

FIELD OF THE INVENTION

The invention is in the field of compositions and methods for inducing natural conception, for example in women unable to conceive, for example due to blocked or damaged fallopian tubes.

BACKGROUND OF THE INVENTION

There is a great need for women to conceive and its importance to women and to society cannot be overstated. Although there are many different causes of a woman experiencing an inability to conceive even when their age and health is appropriate for it to occur, according to one published statistic, over 30 percent of women diagnosed with infertility have damaged or blocked fallopian tubes".

When a woman is having difficulty conceiving naturally, she is asked to undergo imaging tests such as hysterosalpingogram (HSG), an x-ray dye of the uterus and fallopian tubes. The result of the test may show that their fallopian tube(s) are obstructed and/or damaged. The obstruction may be attributed by her OB/GYN physicians to a variety of causes including but not limited to a previous infection, inflammation, previous surgery, ectopic pregnancies, caesarian delivery or other things. This condition—obstruction of the fallopian tube(s), or damage to them, is usually treated through medical procedures or surgeries that may be painful and often unsuccessful. Alternatively, the obstruction is circumvented in that the treating OB/GYN specialist may recommend to the woman to try to conceive through means other than natural means, for example intra vitro fertilization (IVF). However, except in exceptional cases, women strongly prefer to conceive through natural means, as opposed to by means of IVF. Furthermore, women strongly prefer to avoid the above-mentioned surgery.

SUMMARY OF THE EMBODIMENTS

One embodiment is a composition comprising a mixture of:
- a first powder taken from inside a hard, chocolate-brown-colored fruit of a tree, the fruit known as wild Tibet fruit;
- cinnamon powder; and
- turmeric powder, wherein a combination of the cinnamon powder and the turmeric powder constitutes from 10% to 25% by weight of the composition and wherein the first powder constitutes from 75% to 90% by weight of the composition.

In some embodiments, the combination of the cinnamon powder and the turmeric powder constitutes from 12% to 18% by weight of the composition, and wherein the first powder constitutes a remainder of the composition.

In some embodiments, the combination of the cinnamon powder and the turmeric powder constitutes from 14% to 16% by weight of the composition, and wherein the first powder constitutes a remainder of the composition.

In some embodiments, the combination of the cinnamon powder and the turmeric powder constitutes from 14.25% to 15.75% by weight of the composition, and the first powder constitutes from 84.25% to 85.75% of the composition.

Another embodiment is a paste made by mixing water and a powder mixture in a ratio of a milliliter of the water to between 1.33 and 3 grams of the powder mixture, the powder mixture comprising
- a first powder taken from inside a hard, chocolate-brown-colored fruit of a tree, the fruit known as wild Tibet fruit;
- cinnamon powder; and
- turmeric powder.

In some embodiments, a combination of the cinnamon powder and the turmeric powder constitutes from 10% to 25% by weight of the powder mixture and wherein the first powder constitutes from 75% to 90% of the powder mixture.

In some embodiments, a combination of the cinnamon powder and the turmeric powder constitutes from 12% to 18% by weight of the powder mixture, and wherein the first powder constitutes the remainder of the powder mixture.

In some embodiments, a combination of the cinnamon powder and the turmeric powder constitutes from 14% to 16% by weight of the powder mixture, and wherein the first powder constitutes the remainder of the powder mixture.

In some embodiments, a combination of the cinnamon powder and the turmeric powder constitutes from 14.25% to 15.75% by weight of the powder mixture, and the first powder constitutes from 84.25% to 85.75% by weight of the powder mixture.

A further embodiment is a method of treating a condition in a woman, the condition characterized by at least one of the fallopian tubes obstructed in a manner that prevent natural conception, the method comprising vaginally inserting at least 5 grams of a paste wrapped in a porous holder into the woman, the paste made by mixing water and a powder mixture in a ratio such that for every milliliter of the water there is between 1.33 and 3 grams of the powder mixture, the powder mixture comprising
- a first powder taken from inside a hard, chocolate-brown-colored fruit of a tree, the fruit known as wild Tibet fruit;
- cinnamon powder; and
- turmeric powder, wherein a combination of the cinnamon powder and the turmeric powder constitutes from 10% to 25% by weight of the powder mixture and wherein the first powder constitutes from 75% to 90% by weight of the powder mixture.

In some embodiments, the combination of the cinnamon powder and the turmeric powder constitutes from 12% to 18% by weight of the powder mixture, and wherein the first powder constitutes from 82% to 88% by weight of the powder mixture.

In some embodiments, the combination of the cinnamon powder and the turmeric powder constitutes from 14% to 16% by weight of the powder mixture, and wherein the first powder constitutes from 84% to 86% by weight of the powder mixture.

In some embodiments, the combination of the cinnamon powder and the turmeric powder constitutes from 14.25% to 15.75% by weight of the powder mixture, and the first powder constitutes from 84.25% to 85.75% by weight of the powder mixture.

In some embodiments, the paste is made by mixing water and the powder mixture such that for every milliliter of the water there is between 1 and ⅔ and 2 and ⅔ grams of the powder mixture.

In some embodiments, the paste is made by mixing water and the powder mixture such that for every milliliter of the water there is between 2 and 2.3 grams of the powder mixture.

In some embodiments, the paste is made by mixing 3 milliliters of water with 6-7 grams of the powder mixture.

In some embodiments, the paste is administered during selected portions of 4 days commencing one day after the women's menstrual period. In some embodiments, the method further comprises the woman abstaining from sexual relations for 15 days after the 4 day administration of the paste and further comprising resuming sexual relations following the abstinence.

In some embodiments, the paste wrapped in the porous holder is inserted approximately 4-5 centimeters into the woman's vaginal canal.

Another embodiment is a method of preparing a medical device, comprising:

creating a powder mixture by mixing (a) a first powder taken from inside a hard, chocolate-brown-colored fruit of a tree, the fruit known as wild Tibet fruit, together with (b) cinnamon powder and (c) turmeric powder in a ratio of 75%-90% by weight of the first powder and 10%-25% by weight of the combination of cinnamon powder and turmeric powder;

adding water to the powder mixture in a ratio of a milliliter of the water to between 1.33 and 3 grams of the powder mixture to form 5-10 grams of a paste; and placing the paste in a porous holder and tying closed at least one end of the porous holder.

BRIEF DESCRIPTION OF THE DRAWINGS

Various embodiments are herein described, by way of example only, with reference to the accompanying drawings, wherein.

DETAILED DESCRIPTION OF THE EMBODIMENTS

Figure 1:
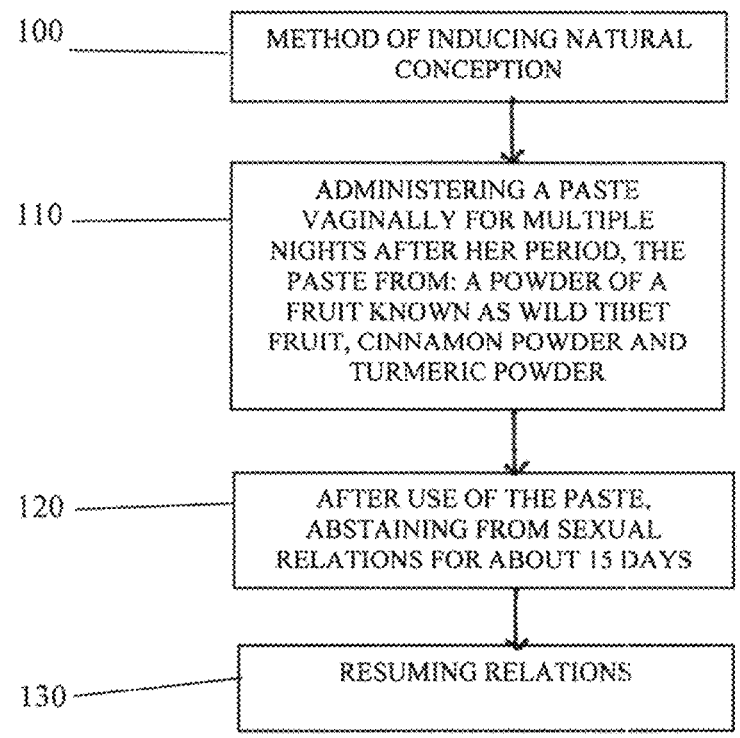
FIG. 1 is a flow chart showing a method, in accordance with one embodiment.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Fallopian tube obstruction can be due to various causes since the tubes are small. Appliant has discovered that by combining certain natural ingredients together, in certain proportions, a syngery is created which clears and heals the fallopian tubes and thereby dramatically increases the likelihood of the woman—previously diagnosed with obstructed or damaged fallopian tubes—to conceive naturally.

The embodiments include compositions and methods that help women conceive naturally in cases in which they have been unable to conceive due to problems with one or more of their fallopian tubes, especially obstructions thereof. One of the compositions is a powder mixture of three powders including a first powder taken from inside a hard, chocolate-brown-colored fruit of a tree, the fruit known as wild Tibet fruit. Another embodiment is a paste made from this powder. Another embodiment is a method of using the paste by administering it vaginally. A further method is a method of preparing the paste and the holder or bandage that holds the paste for its vaginal administration.

Applicant believes that the method and composition described herein for overcoming the problem of the obstructed fallopian tube(s) is applicable to a broad range of causes of the obstruction, including where the obstruction is due to an inflammation.

The principles and operation of a Composition and Method of Inducing Natural Conception may be better understood with reference to the drawings and the accompanying description.

One embodiment is a composition. The composition comprises a mixture of: (i) a first powder taken from the inside of a hard, chocolate-brown-colored fruit that is sometimes called wild Tibet fruit and in Arabic is called Qors Al Qamar or Sin Al Qamar and is sometimes called Kilwa colloquially, (ii) cinnamon powder and (iii) turmeric powder. The fruit may have a diameter of about five centimeters (although this is not a limitation) and grows, among other places, outside of Al Hoceima, a resort city in northern Morocco. The first powder is taken from inside this hard, chocolate-brown colored fruit. The fruit may be somewhat disc-shaped although not flat but rounded (as one goes from the bottom surface to the top surface of the fruit and also the fruit is thicker in its center and therefore leaves the impression of being (slightly) heart-shaped). This hard fruit, when opened up, for example cracked open, reveals a large amount of a whitish powder inside. The whitish powder may appear in hard clumps.

In this patent application the phrase "wild Tibet fruit" and the phrase "fruit known as wild Tibet fruit" each refer to the above-referenced fruit which is the hard, chocolate-brown-colored fruit called in Arabic Qors Al Qamar or Sin Al Qamar and sometimes called wild Tibet fruit and also known sometimes colloquially as Kilwa.

In some embodiments, the proportion of the mixed powder that is the "first powder" (from the fruit) out of the entire powder mixture (of the composition, paste and method herein) is more than 50% and the combination of the second and third powders (cinnamon and turmeric powders) is less than 50% of the entire powder mixture. In some embodiments, the first powder (from the fruit) is two-thirds or more than two-thirds of the entire powder mixture and the combination of the cinnamon power and turmeric powder is one-third or less than one-third of the entire powder mixture.

In one embodiment, the combination of the cinnamon powder and the turmeric powder constitutes from 10% to 25% of the composition and the first powder constitutes from 75% to 90% of the composition.

In one embodiment, the combination of the cinnamon powder and the turmeric powder constitutes from 10% to 20% of the composition and the first powder constitutes from 80% to 90% of the composition.

In one embodiment, the combination of the cinnamon powder and the turmeric powder constitutes from 12% to 18% of the composition, and the first powder constitutes the remainder of the composition.

In one embodiment, the combination of the cinnamon powder and the turmeric powder constitutes from 14% to 16% of the composition, and the first powder constitutes the remainder of the composition.

In one embodiment, the combination of the cinnamon powder and the turmeric powder constitutes from 14.25% to 15.75% of the composition, and the first powder constitutes from 84.25% to 85.75% of the composition.

In other embodiments, the combination of the cinnamon powder and the turmeric powder constitutes from 5% to 30% of the composition and the first powder constitutes from 70% to 95% of the composition.

The powder from these trees were extracted from inside the fruit and this powder was used along with the two other ingredients to create the paste that was used in the method 100 and method 200 described below and in Example 1 and Example 2 described below.

The relative amounts between the cinnamon powder and the turmeric powder may vary. In some embodiments, the cinnamon powder represents from 30% to 70% by weight of the total volume of the cinnamon powder and turmeric powder together, with the turmeric powder representing the remainder. For example, the proportions between the cinnamon powder and the turmeric powder could be for example 30%/70%, 40%/60%, 50%/50%, 60%/40%, 70%/30% or other proportions.

Another embodiment is a paste. The paste is made by mixing water and a powder mixture in a ratio of a milliliter of the water to between 1.33 and 3 grams of the powder mixture. The powder mixture comprises (A) a first powder taken from inside a hard, chocolate-brown-colored (which may be slightly heart-shaped) fruit of a tree, the fruit known as wild Tibet fruit, (B) cinnamon powder and (C) turmeric powder.

In one version of the paste, in regard to the powder mixture of the paste, the first powder (from the fruit) is more than 50% of the entire powder mixture and the combination of the cinnamon power and turmeric powder is less than 50% of the entire powder mixture.

In one version of the paste, in regard to the powder mixture of the paste, the first powder (from the fruit) is two-thirds or more than two-thirds of the entire powder mixture and the combination of the cinnamon power and turmeric powder is one-third or less than one-third of the entire powder mixture.

In one version of the paste, the combination of the cinnamon powder and the turmeric powder constitutes from 10% to 25% of the powder mixture and the first powder constitutes from 75% to 90% of the powder mixture.

In some versions of the paste, the combination of the cinnamon powder and the turmeric powder constitutes from 10% to 20% of the powder mixture and the first powder constitutes from 80% to 90% of the powder mixture.

In one version of the paste, the combination of the cinnamon powder and the turmeric powder constitutes from 12% to 18% of the powder mixture, and the first powder constitutes the remainder of the powder mixture.

In one version of the paste, the combination of the cinnamon powder and the turmeric powder constitutes from 14% to 16% of the powder mixture, and the first powder constitutes the remainder of the powder mixture.

In one version of the paste, the combination of the cinnamon powder and the turmeric powder constitutes from 14.25% to 15.75% of the powder mixture, and the first powder constitutes from 84.25% to 85.75% of the powder mixture.

In other embodiments, the combination of the cinnamon powder and the turmeric powder constitutes from 5% to 30% of the powder mixture and the first powder constitutes from 70% to 95% of the powder mixture.

The relative amounts between the cinnamon powder and the turmeric powder may vary. In some embodiments, the cinnamon powder represents from 30% to 70% by weight of the total volume of the cinnamon powder and turmeric powder together, with the turmeric powder representing the remainder.

As shown in the flow chart of FIG. 1, another embodiment is a method 100 of treating a condition in a woman, the condition characterized by at least one of the fallopian tubes obstructed in a manner that prevent natural conception. Step 110 of this method 100 involves administering a paste vaginally for four consecutive nights after the women's period. The paste is prepared by adding water to the powder mixture described above namely the powder mixture that comprises (a) a first powder taken from the inside of a hard, chocolate-brown-colored fruit known as wild Tibet fruit, cinnamon powder and turmeric powder such that the cinnamon plus turmeric represent 10-25% (in other versions 10%-20%, in other versions 12%-18% and on other versions 14%-16%) of the powder mixture.

Step 110 is implemented, in one version, by vaginally inserting at least 5 grams of a paste wrapped in a porous holder into the woman, the paste made by mixing water and a powder mixture in a ratio such that for every milliliter of the water there is between 1.33 and 3 grams of the powder mixture. The paste may be inserted for multiple nights, for example during four consecutive nights, for example 5-6 hours each night while the woman is sleeping. It is removed in the morning when the woman wakes up.

It should be clear that references in this patent application to "4 days" of administering the paste or a "4 day administration" of the paste or bandage does not mean using the paste or bandage throughout the 24 hours of the day for each of those 4 days but rather during selected portions of those days.

The powder mixture comprises:
(A) a first powder taken from the inside of a hard, chocolate-brown-colored fruit known as wild Tibet fruit;
(B) cinnamon powder;
(C) turmeric powder.

In one version of the method step 110, the combination of the cinnamon powder and the turmeric powder constitutes from 10% to 25% of the powder mixture and the first powder constitutes from 75% to 90% of the powder mixture.

In one version of the method step 110, the combination of the cinnamon powder and the turmeric powder constitutes from 10% to 20% of the powder mixture and the first powder constitutes from 80% to 90% of the powder mixture.

In one version of the method step 110, the combination of the cinnamon powder and the turmeric powder constitutes from 12% to 18% of the powder mixture, and wherein the first powder constitutes from 82% to 88% of the powder mixture.

In one version of the method step 110, the combination of the cinnamon powder and the turmeric powder constitutes from 14% to 16% of the powder mixture, and wherein the first powder constitutes from 84% to 86% of the powder mixture.

In one version of the method step 110, the combination of the cinnamon powder and the turmeric powder constitutes from 14.25% to 15.75% of the powder mixture (or 14.5% to 15.5% in other versions), and the first powder constitutes from 84.25% to 85.75% (or 84.5% to 85.5%) of the powder mixture.

In other embodiments, the combination of the cinnamon powder and the turmeric powder constitutes from 5% to 30% of the powder mixture and the first powder constitutes from 70% to 95% of the powder mixture.

According to one version, the paste is administered at night just prior to the woman's bedtime and is maintained internally during the night while the woman is sleeping and then removed in the morning. The paste may be administered for multiple consecutive nights, for example for 3-5 nights, which may be implemented as four consecutive nights, commencing on the day after the women's menstrual period.

Step 120 of method 100 comprises having the woman abstain from sexual relations for about two weeks, for example about fifteen days, commencing after the four nights of the administration of the paste.

In step 130 of method 100, the woman resumes relations following the abstinence.

The paste wrapped in the porous holder, such as the bandage, is inserted approximately 4-5 centimeters into the woman's vaginal canal. The bandage may be tied to seal an end of the bandage.

In another version of method 100, the powder mixture is mixture of
- a first powder taken from inside a hard, chocolate-brown-colored fruit of a tree, the fruit known as wild Tibet fruit; and
- one or both of:
  - (A) cinnamon powder; and
  - ((B) turmeric powder, wherein one or more of the cinnamon powder and turmeric powder constitutes from 10% to 25% by weight of the composition and wherein the first powder constitutes from 75% to 90% of the composition, in other versions the one or more of the cinnamon powder and the turmeric powder constitutes from 12% to 18% or 14-16% by weight of the composition, and wherein the first powder constitutes a remainder of the composition.

Figure 2:
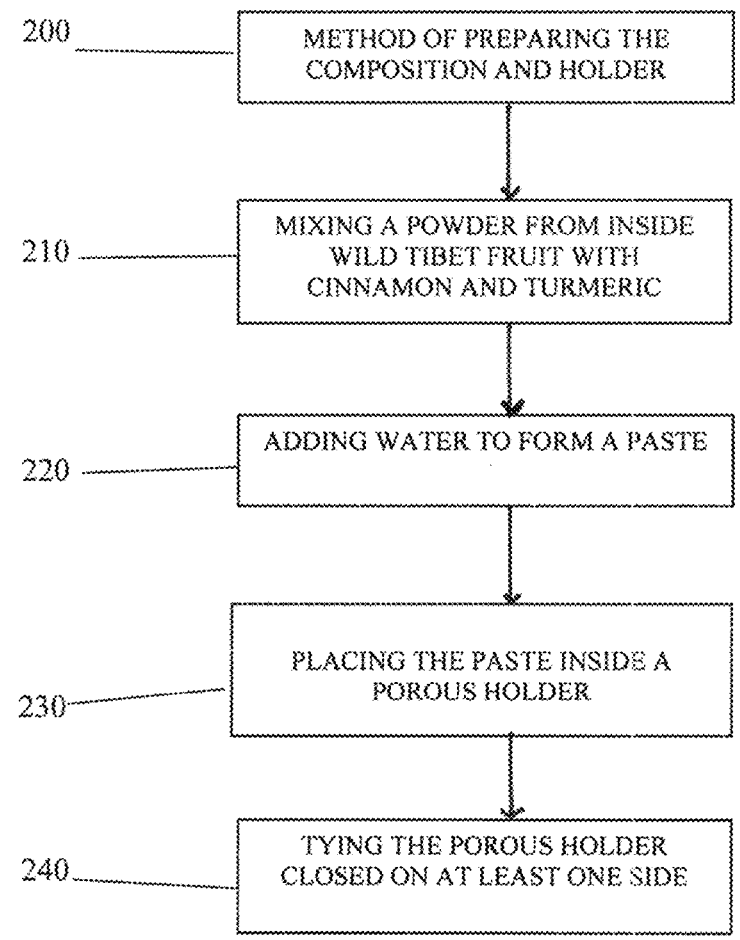
FIG. 2 is a flow chart of a further method, in accordance with one embodiment.

As shown in the flow chart of FIG. 2, another embodiment is a method 200 of making a medical device.

In step 210 of method 200, the paste may be made by mixing a powder mixture that comprises a first powder taken from the inside of a hard, chocolate-brown-colored fruit known as wild Tibet fruit, cinnamon powder and turmeric powder.

In step 220, water is added to the powder mixture to form a paste.

In some eversions of step 220, the water and the powder mixture are combined such that for every milliliter of the water there is between 1 and ⅔ and 2 and ⅔ grams of the powder. In another version of step 220, the paste is made by mixing water and the powder mixture such that for every milliliter of the water there is between 2 and 2.3 grams of the powder mixture. In still another version of the method step 220, the paste is made by mixing 3 milliliters of water with 6-7 grams of the powder mixture.

Step 230 involves placing the paste inside a porous holder such as a bandage that acts as a holder.

Step 240 involves closing the porous holder on at least one side such as by typing the bandage on one end.

Example 1

One woman in her twenties had her first child via Caesarian section. Thereafter, the woman was unable to conceive for three to four years after her first child despite attempting to do so and consulted a physician. The woman consulted with a total of seven physicians who specialize in OB/GYN. In one particular case, after imaging and an hysterosalpingogram, the specialist informed her that one of her fallopian tubes was obstructed and that she would unable to conceive naturally. She was further informed that instead of surgery she should try to become pregnant through In Vitro Fertilization (IVF). This diagnosis and instruction was also told to her previously, or confirmed later, by at least six other physicians who were either professors of medicine and/or specialists in OB/GYN. In the case of the other six physicians the diagnosis was that both of her fallopian tubes were obstructed or damaged. Instead of accepting these physicians' recommendation, the woman used the following method and composition.

The woman vaginally inserted five to ten grams of a paste wrapped in a porous bandage. The paste had been made by mixing three milliliters of water with from 6 grams to 7 grams of a powder mixture. The powder mixture is a mixture of a first powder taken from the inside of a hard, chocolate-brown-colored fruit known as wild Tibet fruit. This first powder constituted 75%-90% of the powder mixture. Cinnamon powder and turmeric powder together constituted the remaining 10%-25% of the powder mixture.

The woman was given this paste (described above in Example One) wrapped in a tied porous holder or bandage and she inserted the holder/bandage approximately four to five centimeters into her vagina leaving it there for each of four consecutive nights, commencing one day after completion of her menstrual period of bleeding. The women inserted the bandage containing the paste just before bedtime each of the four nights and each subsequent morning she removed the holder containing the paste. After the four days of treatment (during the night), she abstained from relations with her husband for a period of fifteen days and resumed relations thereafter. She then conceived approximately two to three months afterwards. She gave birth to a healthy child about nine months later. With no further use of the composition or method, the woman then also gave birth to another healthy child—also through natural conception—in less than two years after the birth of the first child.

Side Effects

During the protocol, one side effect experienced by the woman was that her ovulation was delayed by about 10 days. A further side effect experienced by the woman was that during the nights in which she used the paste in the bandage, she experienced a burning sensation in the vaginal area. The side effects disappeared about a day after treatment.

Example 2

A woman in her 20s had not conceived before after attempting to conceive through natural means for about half a year, underwent an imaging of her uterus. The result of the imaging was that both her fallopian tubes were obstructed. She decided to try the method and composition of described herein.

The woman vaginally inserted 5 to 10 grams of the paste wrapped in a porous bandage. The paste had been made as in Example One. The woman inserted a tied porous bandage and inserted this approximately 4-5 centimeters into her vagina during 4 consecutive nights commencing a day after completion of her menstrual period of bleeding. She then abstained from relations with her husband for fifteen days and resumed relations immediately thereafter. She then conceived approximately three months afterwards. That child was delivered healthy.

Side Effects

This woman experienced two side effects—her ovulation was delayed by about 10 days and during the nights in which she used the paste in the bandage, she experienced a burning sensation in the vaginal area. The side effects disappeared after treatment.

Example 3

A woman in her twenties was, according to her physician, experiencing symptoms from inflammation in the vaginal area. Her physician prescribed a medication. The medication prescribed did not relieve the inflammation and did not help the woman. She decided to try something else. Accordingly, she vaginally inserted approximately 5-10 grams of the paste (the paste described in this patent application and specifically in Example One) wrapped in a porous bandage, the paste made in the manner described throughout this patent application and specifically in the manner described in Example One. The insertion was made approximately 4-5 centimeters into her vagina and this was performed during three consecutive nights. The inflammation disappeared within a few days of the completion of the three nights of administration.

Side Effects

This woman experienced a burning sensation in the vaginal area. The side effects disappeared after treatment.

Another embodiment is a composition comprising a mixture of:
a first powder taken from inside a hard, chocolate-brown-colored fruit of a tree, the fruit known as wild Tibet fruit; and
one or both of:
(A) cinnamon powder; and
((B) turmeric powder,
wherein one or more of the cinnamon powder and turmeric powder constitutes from 10% to 25% by weight of the composition and wherein the first powder constitutes from 75% to 90% of the composition, in other versions the one or more of the cinnamon powder and the turmeric powder constitutes from 12% to 18% or 14-16% by weight of the composition, and wherein the first powder constitutes a remainder of the composition.

Another embodiment is a paste made by mixing water and a powder mixture in a ratio of a milliliter of the water to between 1.33 and 3 grams of the powder mixture, the powder mixture comprising
a first powder taken from inside a hard, chocolate-brown-colored fruit of a tree, the fruit known as wild Tibet fruit; and
one or both of:
(A) cinnamon powder; and
(B) turmeric powder.

In one version of the paste, the one or more of the cinnamon powder and the turmeric powder constitutes from 10% to 25% by weight of the powder mixture and the first powder constitutes from 75% to 90% by weight of the powder mixture.

In another version of the paste, the one or more of the cinnamon powder and the turmeric powder constitutes from 12% to 18% (or 14-16%) by weight of the powder mixture, and wherein the first powder constitutes the remainder of the powder mixture.

While the invention has been described with respect to a limited number of embodiments, it will be appreciated that many variations, modifications and other applications of the invention may be made. Therefore, the claimed invention, as recited in the claims that follow, is not limited to the embodiments described herein.

What is claimed is:

1. A composition comprising a mixture of:
a first powder taken from inside a hard, chocolate-brown-colored fruit of a tree, the fruit known as wild Tibet fruit;
cinnamon powder; and
turmeric powder,
wherein a combination of the cinnamon powder and the turmeric powder constitutes from 10% to 25% by weight of the composition and wherein the first powder constitutes from 75% to 90% of the composition, wherein the composition is in a form, and in a therapeutically effective amount, for treatment of a condition of a woman having at least one blocked or damaged fallopian tube.

2. The composition of claim 1, wherein the combination of the cinnamon powder and the turmeric powder constitutes from 12% to 18% by weight of the composition, and wherein the first powder constitutes a remainder of the composition.

3. The composition of claim 1, wherein the combination of the cinnamon powder and the turmeric powder constitutes from 14% to 16% by weight of the composition, and wherein the first powder constitutes a remainder of the composition.

4. The composition of claim 1, wherein the combination of the cinnamon powder and the turmeric powder constitutes from 14.25% to 15.75% by weight of the composition, and the first powder constitutes from 84.25% to 85.75% by weight of the composition.

5. A paste made by mixing water and a powder mixture in a ratio of a milliliter of the water to between 1.33 and 3 grams of the powder A mixture, the powder mixture comprising:
a first powder taken from inside a hard, chocolate-brown-colored fruit of a tree, the fruit known as wild Tibet fruit;
cinnamon powder; and
turmeric powder,
wherein the paste is in a therapeutically effective amount for treatment of a condition of a woman having at least one blocked or damaged fallopian tube.

6. The paste of claim 5, wherein a combination of the cinnamon powder and the turmeric powder constitutes from 10% to 25% by weight of the powder mixture and wherein the first powder constitutes from 75% to 90% by weight of the powder mixture.

7. The paste of claim 5, wherein a combination of the cinnamon powder and the turmeric powder constitutes from 12% to 18% by weight of the powder mixture, and wherein the first powder constitutes the remainder of the powder mixture.

8. The paste of claim 5, wherein a combination of the cinnamon powder and the turmeric powder constitutes from 14% to 16% by weight of the powder mixture, and wherein the first powder constitutes the remainder of the powder mixture.

9. The paste of claim 5, wherein a combination of the cinnamon powder and the turmeric powder constitutes from 14.25% to 15.75% by weight of the powder mixture, and the first powder constitutes from 84.25% to 85.75% by weight of the powder mixture.

10. A method of treating a condition in a woman, the condition characterized by at least one of the fallopian tubes obstructed in a manner that prevent natural conception, the method comprising: vaginally inserting a therapeutically effective amount of a composition comprising at least five to ten grams of a paste wrapped in a porous holder into the woman, the paste made by mixing water and a powder mixture in a ratio such that for every milliliter of the water there is between 1.33 and 3 grams of the powder mixture, the powder mixture comprising
a first powder taken from inside a hard, chocolate-brown-colored fruit of a tree, the fruit known as wild Tibet fruit;
cinnamon powder; and
turmeric powder, wherein a combination of the cinnamon powder and the turmeric powder constitutes from 10% to 25% of the powder mixture and wherein the first powder constitutes from 75% to 90% by weight of the powder mixture.

11. The method of claim 10, wherein the combination of the cinnamon powder and the turmeric powder constitutes from 12% to 18% by weight of the powder mixture, and wherein the first powder constitutes from 82% to 88% by weight of the powder mixture.

12. The method of claim 10, wherein the combination of the cinnamon powder and the turmeric powder constitutes from 14% to 16% by weight of the powder mixture, and wherein the first powder constitutes from 84% to 86% by weight of the powder mixture.

13. The method of claim 10, wherein the combination of the cinnamon powder and the turmeric powder constitutes from 14.25% to 15.75% by weight of the powder mixture, and the first powder constitutes from 84.25% to 85.75% by weight of the mixture powder.

14. The method of claim 10, wherein the paste is made by mixing water and the powder mixture such that for every milliliter of the water there is between 1 and 2/3 and 2 and 2/3 grams of the powder mixture.

15. The method of claim 10, wherein the paste is made by mixing water and the powder mixture such that for every milliliter of the water there is between 2 and 2.3 grams of the powder mixture.

16. The method of claim 10, wherein the paste is made by mixing 3 milliliters of water with 6-7 grams of the powder mixture.

17. The method of claim 10, wherein the paste is administered during selected portions of 4 days commencing one day after the women's menstrual period.

18. The method of claim 17, further comprising the woman abstaining from sexual relations for 15 days after the 4 day administration of the paste and further comprising resuming sexual relations following the abstinence.

19. The method of claim 10, wherein the paste wrapped in the porous holder is inserted approximately 4-5 centimeters into the woman's vaginal canal.

20. A method of preparing a medical device, comprising:

creating a powder mixture by mixing (a) a first powder taken from inside a hard, chocolate-brown-colored fruit of a tree, the fruit known as wild Tibet fruit, together with (b) cinnamon powder and (c) turmeric powder in a ratio of 80%-90% by weight of the first powder and 10%-20% by weight of the combination of cinnamon powder and turmeric powder;

adding water to the powder mixture in a ratio of a milliliter of the water to between 1.33 and 3 grams of the powder mixture to form 5-10 grams of a paste; and placing the paste in a porous holder and tying closed at least one end of the porous holder, wherein the paste is in a therapeutically effective amount for treatment of a condition of a woman having at least one blocked or damaged fallopian tube.

* * * * *